United States Patent [19]

Nakamori

[11] Patent Number: 5,894,128
[45] Date of Patent: Apr. 13, 1999

[54] INFRARED TYPE GAS ANALYZER

[75] Inventor: Akioki Nakamori, Kyoto, Japan

[73] Assignee: Shimadzu Corporation, Kyoto, Japan

[21] Appl. No.: 08/917,474

[22] Filed: Aug. 26, 1997

[30] Foreign Application Priority Data

Sep. 6, 1996 [JP] Japan ................ 8-236804

[51] Int. Cl.$^6$ ................ G01N 21/61
[52] U.S. Cl. ................ 250/343; 250/344; 250/252.1 A
[58] Field of Search ................ 250/343, 345, 250/344, 252.1 A, 339.13; 356/437, 439

[56] References Cited

U.S. PATENT DOCUMENTS

| | | | |
|---|---|---|---|
| 4,746,218 | 5/1988 | Lord, III | 356/437 |
| 4,885,469 | 12/1989 | Yamagishi et al. | 250/343 |
| 5,060,505 | 10/1991 | Tury et al. | 250/343 |
| 5,077,469 | 12/1991 | Fabinski et al. | 250/345 |
| 5,206,511 | 4/1993 | Apperson et al. | 250/252.1 |

*Primary Examiner*—Edward P. Westin
*Assistant Examiner*—Richard Hanig
*Attorney, Agent, or Firm*—Kanesaka & Takeuchi

[57] ABSTRACT

An infrared type gas analyzer is formed of a measuring cell for receiving a gas to be measured; an infrared light source for irradiating the gas in the measuring cell; a correlation filter disposed adjacent to the measuring cell; and a sensor for detecting infrared light ejected from the infrared light source and passing through the correlation filter and the measuring cell to analyze the gas in the measuring cell. A correction filter is disposed on a portion of the correlation filter for correction or calibration of the gas analyzer. Thus, the infrared type gas analyzer has a simple structure and can perform a simplified correction without complicated operation.

7 Claims, 4 Drawing Sheets

INFRARED TYPE GAS ANALYZER

BACKGROUND OF THE INVENTION AND RELATED ART STATEMENT

The present invention relates to an infrared type gas analyzer, in particular an infrared type gas analyzer with a correlation filter for continuously measuring a concentration of a specific component in a gas or vapor by utilizing an infrared absorption effect which is an inherent characteristic of gas molecules.

FIG. 4 is a block diagram for showing a CO analyzer which is an example of an infrared type gas analyzer provided with a conventional correlation filter. In the infrared type gas analyzer, infrared light from a light source 11 is irradiated to a measuring cell 13 through a gas correlation filter 120 The measuring cell 13 includes an introduction port 13a and a discharge port 13b so that a sample gas can continuously flow. An optical filter 13c disposed on a front face of the measuring cell 13 permits only the infrared light in a CO absorption wavelength range to pass therethrough, so that an interference error by a gas component close to the CO absorption wavelength range, such as $CO_2$, can be removed.

As shown in FIG. 5, the gas correlation filter 12 includes a CO cell 12a containing a CO gas to be measured, and an $N_2$ cell 12b containing an $N_2$ gas, so called zero gas, not absorbing the infrared light, and is appropriately driven by a motor 14 shown in FIG. 4.

A sensor 15 alternately detects the infrared light obtained through the CO cell 12a and the infrared light obtained through the $N_2$ cell 12b, and a data processing section 16 calculates a CO concentration in the sample gas from the alternately detected data.

More specifically, since the infrared light in the CO absorption wavelength range is completely absorbed from the infrared light passing through the CO cell 12a, a component in the CO absorption wavelength range of the infrared light in the data detected by the sensor 15 becomes zero regardless of a CO concentration in the measuring cell 13. On the other hand, data detected by the sensor 15 of the infrared light transmitted through the $N_2$ cell 12b becomes a value corresponding to the CO concentration in the measuring cell 13 since the component in the CO absorption wavelength range remains as it is. Therefore, the CO concentration in the sample gas can be obtained by calculating a ratio of both the values at the data processing section 16.

In the infrared type gas analyzer as described above, a zero value and a measuring range, i e. span, are required to be periodically corrected by using a standard for comparisons Heretofore, a zero-point or span-point has been corrected or calibrated by flowing a zero gas or span gas instead of a gas to be measured during the measurement by using electromagnetic valves or the like. Therefore, since the correction gas is released to the atmosphere in succession, consumption of the correction gas is extremely increased in comparison with other gas analyzers to thereby raise a correction cost.

Therefore, it has been practiced that at a time of a span correction, a correction gas is not used, and instead, an amount of the infrared light is adjusted by providing a light regulating plate or douser in a light path of the infrared ray to coincide with an amount of the infrared light reaching the sensor without being absorbed by a gas having a known concentration when the gas is caused to flow. More specifically, in case a zero correction of the gas analyzer is carried out, a zero gas is applied to flow through the measuring cell to perform the zero correction. Then, in case a span correction is carried out, the zero gas is applied to flow through the measuring cell, as in the zero correction, and the span correction is carried out in a state where the light regulating plate is inserted into the infrared light path to precisely coincide therewith. Incidentally, it is necessary that an output value of the light regulating plate is beforehand confirmed by the span gas, because the output value at this time becomes a correction value.

Also, an optical filter or a filter containing a gas therein may be used instead of the light regulating plate.

In the conventional infrared type gas analyzer, the zero and span corrections are carried out as described hereinabove. However, there have been defects such that mechanisms for moving the light regulating plate and optical filter are required to thereby complicate a structure of the infrared type gas analyzer. Also, when the light regulating plate or optical filter is repeatedly moved, it must be placed at a position precisely coinciding with the infrared light path. Thus, a position detector is also required to thereby complicate the structure.

In view of the foregoing, the present invention has been made, and an object of the present invention is to provide an infrared type gas analyzer having a simple structure by which a correction or calibration can be simply carried out without complicated operations.

Further objects and advantages of the invention will be apparent from the following description of the invention

SUMMARY OF THE INVENTION

An infrared type gas analyzer of the invention is used for process control of a gas concentration at a chemical plant and iron works; analysis of a flue gas from a boiler and combustion furnace, monitoring of air pollution; measurement of exhaust gas from cars or the like. The infrared type gas analyzer is basically formed of an infrared light source, a correlation filter, a measuring cell, and a sensor.

According to a first aspect of the present invention, in the infrared type gas analyzer, an infrared light is irradiated to the measuring cell, into which a sample gas is introduced, through the correlation filter, and the infrared light transmitted through the measuring cell is detected by the sensor to analyze a specific gas component. In the invention, the correlation filter is provided with an optical filter, or a light regulating plate or douser for making a simplified correction.

According to a second aspect of the present invention, in the infrared type gas analyzer, the correlation filter is provided with a gas filter for making a simplified correction, The infrared type gas analyzer of the present invention is structured as described above, and in case the correction is carried out, a portion of the correlation filter on which the optical filter or the light regulating plate is attached, or the gas filter is provided, is located in a light path to obtain the same situation as in a case where a span gas is caused to flow through the measuring cell. Thus, the correction can be carried out simply without using any mechanism for moving the light regulating plate and a position detector.

DETAILED DESCRIPTION OF PREFERRED EMBODIMENTS

Figure 1:
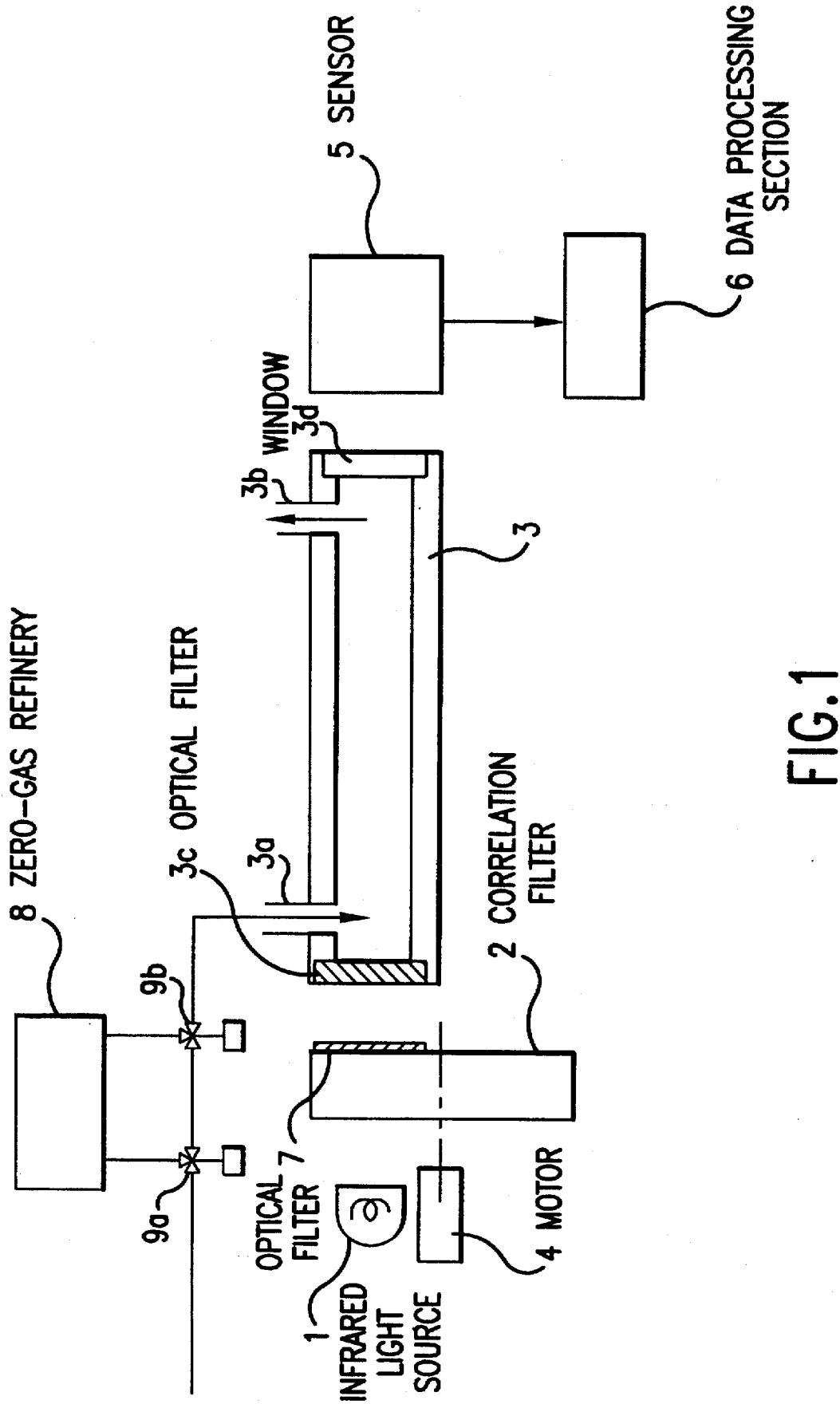
FIG. 1 is a block diagram for showing an embodiment of an infrared type gas analyzer of the invention.
Figure 4:
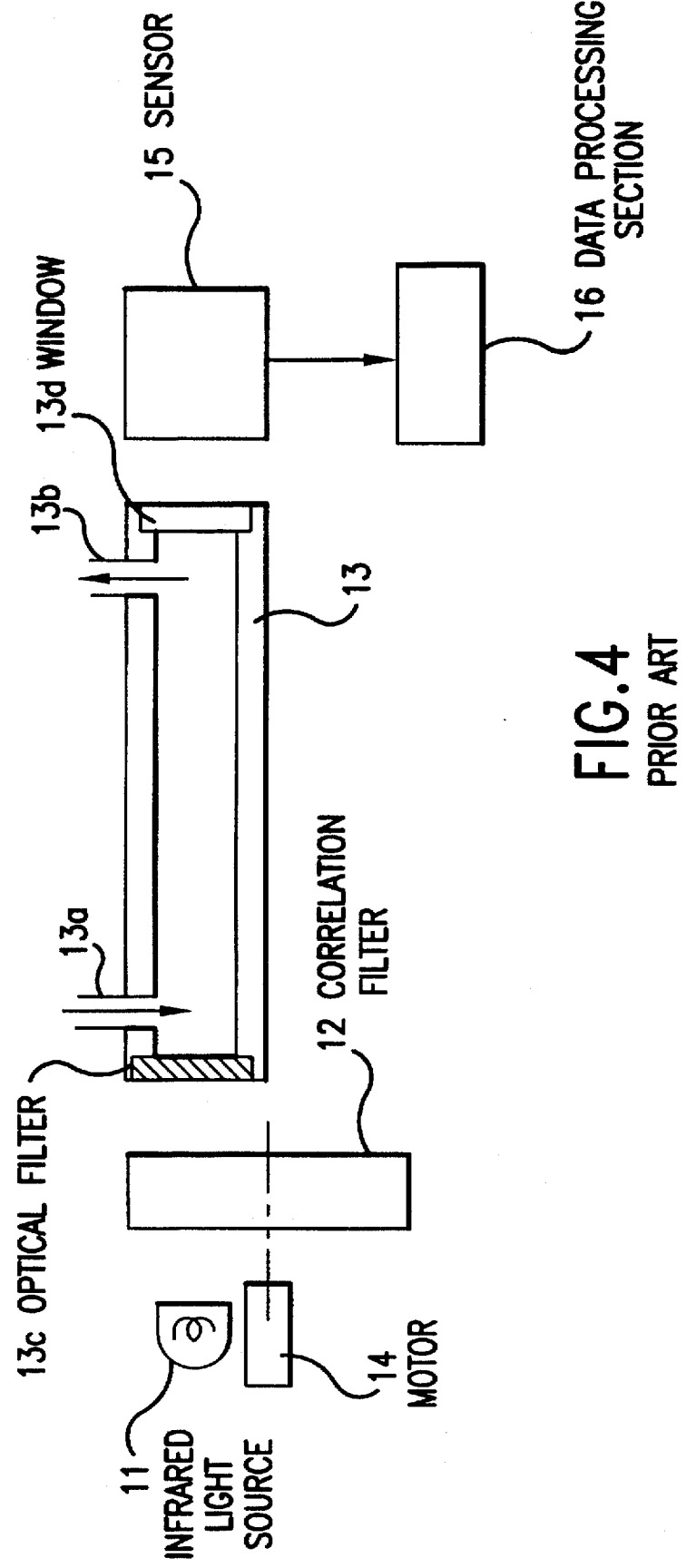
FIG. 4 is a block diagram for showing a conventional infrared type gas analyzer.
Figure 5:
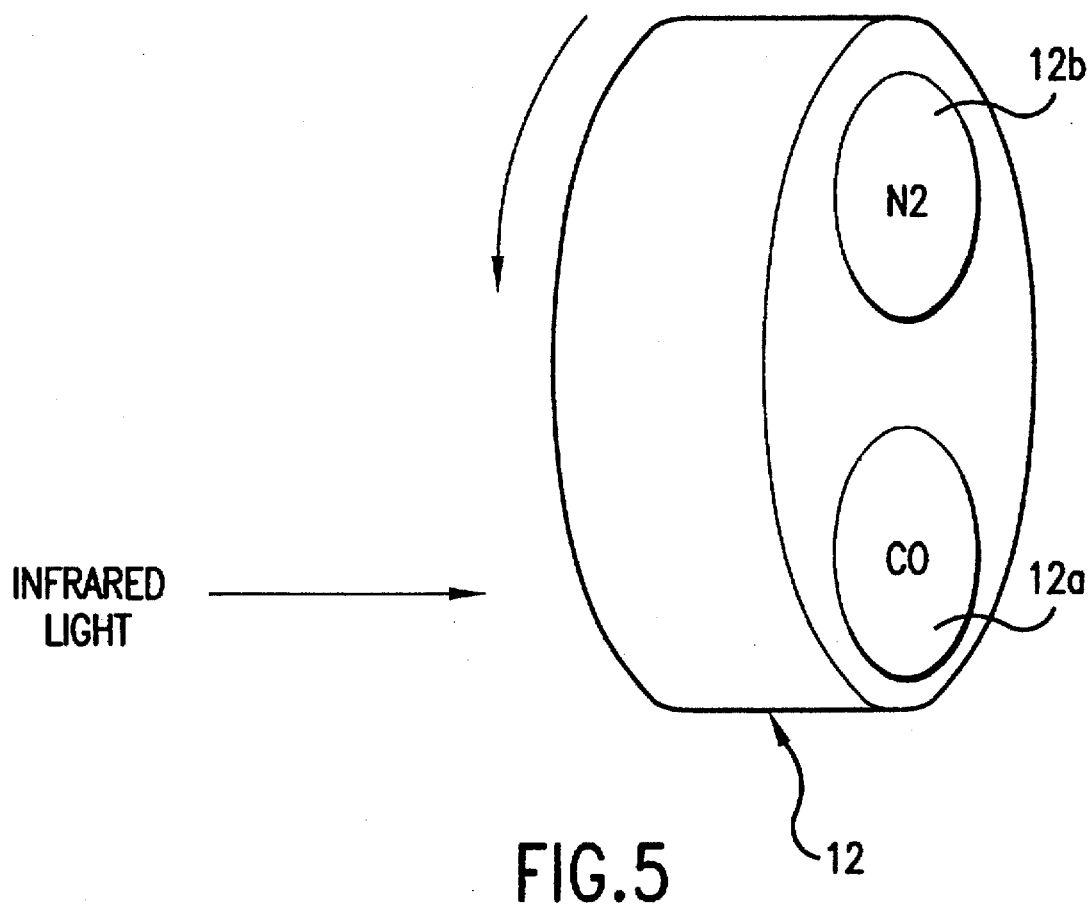
FIG. 5 is a perspective view for showing a correlation filter for the conventional infrared type gas analyzer.

FIG. 1 is a schematic view of an infrared type gas analyzer according to the present invention. The infrared type gas analyzer basically includes an infrared light source 1, a correlation filter 2, a measuring cell 3, a motor 4, a sensor 5, a data processing section 6, a zero-gas refinery 8 and electromagnetic valves 9a, 9b, similar to an infrared type gas analyzer shown in FIG. 4. An optical filter 7 is attached onto a portion of a surface of the correlation filter 2. The measuring cell 3 includes an introduction port 3a and a discharge port 3b, so that a sample gas can flow continuously. The infrared light passing through the correlation filter 2 and an optical filter 3c passes through the sample gas in the measuring cell 3, and reaches the sensor 5 through a window 3d. The optical filter 3c permits only the infrared light in the CO absorption wavelength range to pass therethrough, as in the infrared type gas analyzer shown in FIG. 4.

The sensor 5 detects individually infrared strengths in a wavelength range absorbing a specific gas component, i.e. carbon monoxide in the present embodiment, and outputs to the data processing section 6. The sensor 5 used in the present embodiment is an infrared sensor, such as a PbSe sensor and a pyroelectric sensor. The data processing section 6 calculates a concentration of an object gas to be measured from the detected data of the infrared lights passing through a cell containing therein the object gas and a cell containing therein a zero-gas of the correlation filter 2, respectively, as in the conventional method.

Figure 2:
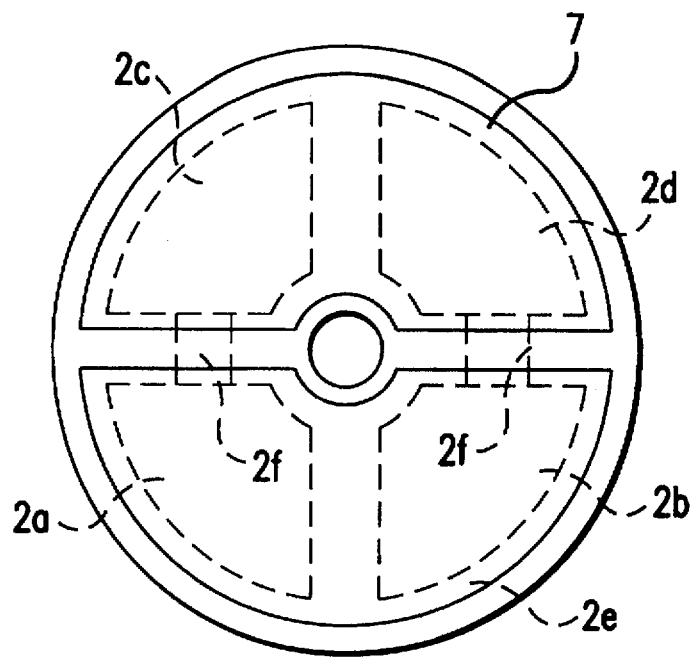
FIG. 2 is a front view for showing an embodiment of a correlation filter to be used in the infrared type gas analyzer of the invention.

FIG. 2 shows an embodiment of a structure of the correlation filter. The correlation filter 2 includes CO cells 2a, 2c for sealing therein a CO gas and $N_2$ cells 2b, 2d for sealing therein a zero-gas ($N_2$) which does not absorb the infrared light. These CO and $N_2$ cells are disposed to be approximately equally spaced apart from each other, and formed in the same shape.

An optical filter 7, which permits only a certain amount of the infrared ray in the CO absorption wavelength range to pass therethrough, is attached onto one surface of an upper half of the correlation filter 2, i.e. CO cell 2c and the $N_2$ cell 2d as shown in FIG. 2. An amount of the infrared ray passing through the optical filter 7 is adjusted to coincide with an amount of light of the infrared ray which reaches the sensor without being absorbed by a correction gas having a known concentration when the correction gas flows. Also, a window material 2e for keeping gases therein is attached on a lower half of the correlation filter 2. Incidentally, the CO cells 2a, 2c and $N_2$ cells 2b, 2d are connected through communication holes 2f in the interior, respectively Thus, the gas can be supplied and sealed respectively by one operation to simplify the gas supplying and sealing operation.

Next, a method for using the infrared type gas analyzer of the invention is explained. In case a measurement is carried out, a sample gas is introduced into the measuring cell 3 and the motor 4 is actuated, so that the CO cell 2a and $N_2$ cell 2b disposed in the correlation filter 2 are sequentially positioned on the optical filter 3c of the measuring cell 3, and the infrared lights passing through the respective cells and measuring cell 3 are sequentially detected by the detector 5.

In the infrared light passing through the CO cell 2a, the light having wavelength in the CO absorption range is completely absorbed. Thus, in the data detected by the sensor 5, the component in the CO absorption wavelength range of the infrared light becomes zero, regardless of a concentration of CO in the measuring cell 3. In the infrared light passing through the $N_2$ cell 2b, the infrared light in the CO absorption range remains as it is, the data detected by the sensor 5 becomes a value corresponding to the CO concentration in the measuring cell 3.

Therefore, the CO concentration in the sample gas can be calculated at the data processing section 6 from a ratio of the detected values of the infrared lights in the CO absorption wavelength range passing through the CO cell 2a and the $N_2$ cell 2b.

When a correction is carried out, the electromagnetic valves 9a, 9b are shifted so that a flow path is changed to the zero-gas refinery 8 to let a zero gas flow into the measuring cell 3. Then, first, as in the regular measuring procedure, the motor 4 is actuated so that the CO cell 2a and the $N_2$ cell 2b disposed in the correlation filter 2 are sequentially positioned on the optical filter 3c of the measuring cell 3; the infrared lights having been transmitted through the respective cells and the measuring cell 3 are sequentially detected by the sensor 5, and a zero correction is carried out by using a ratio of the detected values of the infrared lights in the absorption wavelength range of the detected CO.

Next, the motor 4 is actuated so that the CO cell 2c and the $N_2$ cell 2d disposed in the correlation filter 2 are sequentially positioned on the optical filter 3c of the measuring cell 3. Then, the infrared lights passing through the respective cells 2c, 2d, optical filter 7 and measuring cell 3 are sequentially detected by the sensor 5. At this time, since the infrared light passing through the $N_2$ cell 2d and the optical filter 7 coincides with an amount of light of the infrared ray reaching the detector 5 without being absorbed by a gas having a known concentration when the gas flows, a span correction can be carried out from a ratio of both the detected signals.

Figure 3:
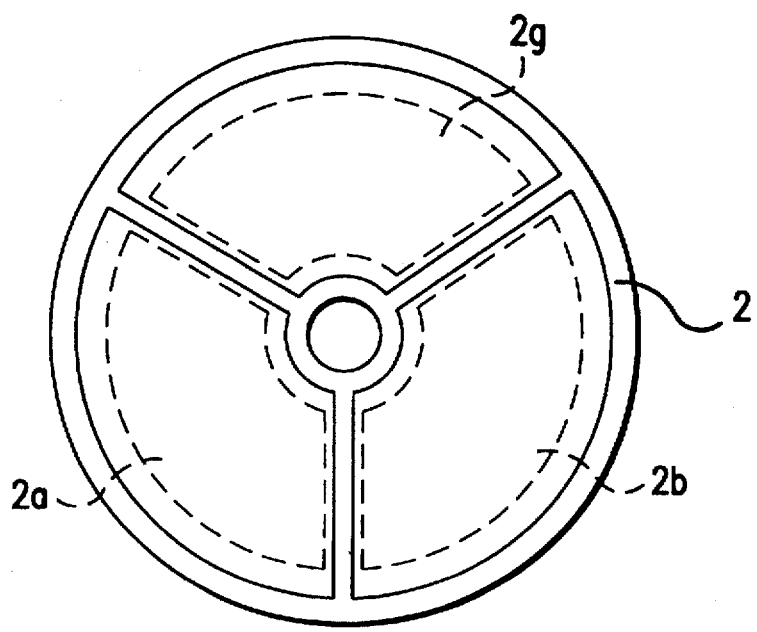
FIG. 3 is a front view for showing another embodiment of a correlation filter to be used in the infrared type gas analyzer of the invention.

Incidentally, in the above embodiment, although the optical filter is attached onto a part of the surface of the correlation filter, a light regulating plate or douser may be attached thereon instead of the optical filter. Also, as shown in FIG. 3, a simplified correction can be carried out similarly by providing a gas filter 2g containing therein a correction gas having a known concentration to the correlation filter 2.

Also, in the above embodiment, the portion where the optical filter 7 is attached is provided with the CO cell 2c. However, since the correction can also be carried out by using the CO cell 2a, the CO cell 2c may not be provided. Further, although the correlation filter 2 is provided between the light source 1 and the measuring cell 3, the filter 2 may be disposed between the measuring cell 3 and the sensor 5.

According to the present invention, a simplified span correction can be simply carried out by only attaching an optical filter or light regulating plate on a correlation filter, or providing a gas filter thereon, so that any mechanism for moving the light regulating plate or the optical filter is not required. Also, since a position detector required when the light regulating plate or optical filter is moved is not necessary, the span correction can be easily carried out with a simple structure.

While the invention has been explained with reference to the specific embodiments of the invention, the explanation is illustrative, and the invention is limited only by the appended claims.

What is claimed is:

1. An infrared type gas analyzer comprising:
   a measuring cell for receiving a gas to be measured;
   an infrared light source for irradiating the gas in the measuring cell;
   a correlation filter disposed adjacent to the measuring cell;
   a sensor for detecting infrared light ejected from the infrared light source and passing through the correlation filter and the measuring cell to analyze the gas in the measuring cell; and
   a correction filter disposed on a portion of the correlation filter for correction of the gas analyzer.

2. An infrared type gas analyzer according to claim 1, wherein said correction filter is selected from a group consisting of an optical filter, a light regulating plate and a gas filter having a correction gas with a known concentration, said correction filter allowing only a certain amount of the infrared light to pass therethrough.

3. An infrared type gas analyzer according to claim 2, wherein said correlation filter includes two pairs of cells, one pair thereof being covered by said optical filter.

4. An infrared type gas analyzer according to claim 3, wherein said correlation filter includes two pairs of CO cells and $N_2$ cells therein.

5. An infrared type gas analyzer according to claim 2, wherein said correlation filter includes a CO cell, an $N_2$ cell and the gas filter having therein a correction gas with a known concentration.

6. An infrared type gas analyzer according to claim 2, wherein the measuring cell includes an introduction port and a discharge port so that the gas to be measured is continuously introduced therein.

7. An infrared type gas analyzer according to claim 6, further comprising a motor for driving the correlation filter to be aligned with an optical filter of the measuring cell, and a data processor connected to the sensor for calculating a concentration of the gas from data detected by the sensor.

* * * * *